US007132552B2

(12) United States Patent
Dolitzky et al.

(10) Patent No.: US 7,132,552 B2
(45) Date of Patent: Nov. 7, 2006

(54) PROCESS FOR PRODUCING LEVETIRACETAM

(75) Inventors: Ben-Zion Dolitzky, Petah Tiqva (IL); Jean Hildesheim, Mazkeret Batya (IL); Serguei Finogueev, Qiriat Arabaa (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 10/771,821

(22) Filed: Feb. 3, 2004

(65) Prior Publication Data

US 2004/0259933 A1    Dec. 23, 2004

Related U.S. Application Data

(60) Provisional application No. 60/455,795, filed on Mar. 19, 2003, provisional application No. 60/444,550, filed on Feb. 3, 2003.

(51) Int. Cl.
*C07D 207/277* (2006.01)

(52) U.S. Cl. ........................ 548/543; 548/550
(58) Field of Classification Search ................ 548/550, 548/543
See application file for complete search history.

(56) References Cited

U.S. PATENT DOCUMENTS

| 4,069,336 | A | * | 1/1978 | Lange et al. ................ 514/422 |
| 4,145,347 | A | * | 3/1979 | L'Italien et al. ............. 546/208 |
| 4,696,943 | A | * | 9/1987 | Gobert et al. ................ 514/424 |
| 4,837,223 | A | * | 6/1989 | Gobert et al. ................ 514/424 |
| 6,107,492 | A | * | 8/2000 | Futagawa et al. ............ 548/543 |
| 6,713,635 | B1 | * | 3/2004 | Surtees et al. ............... 548/550 |
| 2004/0116507 | A1 | * | 6/2004 | Differding et al. ........... 514/424 |

FOREIGN PATENT DOCUMENTS

| GB | 1309692 | | 3/1973 |
| GB | 2225322 | A * | 5/1990 |
| WO | WO 200164637 | A1 * | 9/2001 |
| WO | WO 2003014080 | A2 * | 2/2003 |
| WO | WO 2004076416 | A1 * | 9/2004 |

OTHER PUBLICATIONS

J.P. Michael and D. Gravestock, "Vinylogous Urethanes in Alkaloid Synthesis" *J.Chem.Soc.,Perkin Trans.* 1, 2000, 1919-1928.
E. Carceller, et al., "Synthesis and Structure-Activity Relationships of 1-Acyl-4-((2-Methyl-3-Pyridyl)Cyanomethyl)Piperazines AsPAF Antagonists" *J.Med.Chem.*, 1993, 36, 2984-2997.

* cited by examiner

*Primary Examiner*—Kamel A. Saeed
*Assistant Examiner*—Susannah L. Chung
(74) *Attorney, Agent, or Firm*—Kenyon & Kenyon LLP

(57) ABSTRACT

The invention relates to a method of making optically and chemically pure levetiracetam and to the levetiracetam produced by such process.

26 Claims, No Drawings

PROCESS FOR PRODUCING LEVETIRACETAM

CROSS-REFERENCE TO RELATED APPLICATION

This application claims the benefit under 35 U.S.C. § 1.119(e) of Provisional Application Ser. No. 60/444,550 filed Feb. 3, 2003 and Provisional Application No. 60/455,795, filed Mar. 19, 2003, the disclosures of which are incorporated by reference in its entirety herein.

FIELD OF THE INVENTION

The invention relates to a process for producing optically and chemically pure levetiracetam.

BACKGROUND OF THE INVENTION

Levetiracetam is an antiepileptic drug indicated as adjunctive treatment of partial onset seizures in adults with epilepsy. The chemical name for levetiracetam, a single enantiomer, is (S)-α-ethyl-2-oxo-1-pyrrolidineacetamide.

British Pat. No. 1,309,692 describes the compound α-ethyl-2-oxo-1-pyrrolidineactamide (melting point 122 degrees C.) and states that compounds of this type can be used for therapeutic purposes, for example for the treatment of motion sickness, hyperkinesia, hypertonia and epilepsy. Moreover, it also mentions that these compounds can be applied in the field of memory disorders in normal or pathological conditions.

It is also known that α-ethyl-2-oxo-1-pyrrolidineacetamide possesses a protective activity against aggressions of the central nervous system caused by hypoxias, cerebral ischemia, etc. (Pharmazie, 37/11, (1982), 753–765).

U.S. Pat. No. 4,696,943 discloses the levorotatory isomer of α-ethyl-2-oxo-1-pyrrolidineacetamide, which has the absolute S configuration, a method for making the isomer and pharmaceutical compositions containing the same. U.S. Pat. No. 4,696,943 discloses that the levorotatory isomer has a 10 times higher protective activity against hypoxia and a 4 times higher protective activity against ischemia compared to the known racemic form.

SUMMARY OF THE INVENTION

The invention provides a process for making levetiracetam, levetiracetam produced by the process of the invention and pharmaceutical compositions containing levetiracetam. The process entails reacting (S)-2-amino-butanamide hydrochloride and 4-chlorobutyryl chloride in acetonitrile or methyl tert-butyl ether, in the presence of a strong base, and recovering the crude levetiracetam. Unlike the prior art, the process does not require a catalyst, such as tetrabutylammonium bromide. The process is a one step condensation reaction in which acetonitrile or methyl tert-butyl ether is used as the reaction solvent. The process may enable the production of levetiracetam of high chemical purity, i.e., having less than 0.2% impurities in the crude product and less than 0.1% impurities in the crystallized product.

DETAILED DESCRIPTION OF THE INVENTION

The terms "crystallization" and "recrystallization" as used herein include the dissolution of the material and the isolation of either the crude material, the crystallized material or the recrystallized material.

In one aspect, the invention provides a process for preparing (S)-α-ethyl-2-oxo-1-pyrrolidineacetamide (levetiracetam) comprising reacting (S)-2-amino-butanamide hydrochloride and 4-chlorobutyryl chloride in acetonitrile, in the presence of a strong base, and recovering the crude levetiracetam.

In another aspect, the invention provides a process for preparing (S)-α-ethyl-2-oxo-1-pyrrolidineacetamide (levetiracetam) comprising reacting (S)-2-amino-butanamide hydrochloride and 4-chlorobutyryl chloride in methyl tert-butyl ether, in the presence of a strong base, and recovering the crude levetiracetam.

In a third aspect, the invention provides a process for preparing (S)-alpha-ethyl-2-oxo-1-pyrrolidineacetamide which comprises cyclizing (S)-N-[1-(aminocarbonyl)propyl]-4-chlorobutanamide, in a solvent selected from the group consisting of acetonitrile and methyl tert-butyl ether, in the presence of a strong base.

In a fourth aspect, the invention provides a process for preparing (S)-alpha-ethyl-2-oxo-1-pyrrolidineacetamide which comprises cyclizing (S)-N-[1-(aminocarbonyl)propyl]-4-chlorobutanamide, in the presence of a strong base and in the absence of a catalyst.

In a fifth aspect, the invention provides a process for preparing (S)-α-ethyl-2-oxo-1-pyrrolidineacetamide (levetiracetam) comprising reacting (S)-2-amino-butanamide hydrochloride and 4-chlorobutyryl chloride, in an inert solvent, in the absence of a catalyst, and recovering the crude levetiracetam. The reaction preferably takes place in the presence of a strong base. The inert solvent is preferably acetonitrile or methyl tert-butyl ether.

The strong base used in the processes may be any that is known in the art, but is preferably sodium hydroxide or potassium hydroxide. Preferably, the strong base is present in an amount of at least about 3 molar equivalents based on the amount of (S)-2-amino-butanamide hydrochloride. In other words, for each mole of (S)-2-amino-butanamide hydrochloride, there is at least 3 moles of strong base.

The term "catalyst" as used herein includes 2-hydroxypyridine and phase transfer catalysts such as tetrabutylammonium bromide, tetrabutylammonium iodide, tetrabutylammonium hydrogen sulphate, tetraethylammonium bromide, triethyl benzyl ammonium bromide, tributyl methyl ammonium chloride, tributyl ethyl ammonium chloride, triethyl butyl ammonium chloride, tetra methyl ammonium chloride, tetra methyl iodide, etc.

The reaction temperature for the processes is preferably maintained at between about −15 degrees Celsius and about +25 degrees Celsius, more preferably between about −15 degrees Celsius and about +15 degrees Celsius, even more preferably between about −15 degrees Celsius and +10 degrees Celsius, and most preferably between about 0 degrees Celsius and +5 degrees Celsius.

The reaction preferably takes place in the presence of a drying agent. Examples of drying agents that may be used include magnesium sulphate, molecular sieves, potassium carbonate, sodium carbonate, or sodium sulphate. The drying agent is preferably sodium sulfate.

The pH of the completed reaction mixture is preferably adjusted to less than about 8, more preferably to less than about 7. The pH may be adjusted before or after filtration of the reaction mixture.

The crude levetiracetam may be purified by crystallization or recrystallization from an organic solvent or a mixture of organic solvents. The organic solvent is perferably an alcohol, a ketone, a hydrocarbon, an ether, an ester or mixtures thereof. Examples of alcohols that may be used include isopropyl alcohol, ethanol, methanol, butanol or mixtures thereof. Examples of ketones that may be used include methyl ethyl ketone, methyl isobutyl ketone, or mixtures thereof. Examples of hydrocarbons that may be used include toluene, hexane, or mixtures thereof. Examples of ethers that may be used include methyl tert-butyl ether. Examples of esters that may be used include isobutyl acetate, ethyl acetate or mixtures thereof.

The processes according to the invention may enable the production of crude levetiracetam having a high optical purity, i.e., comprising less than about 0.4% by weight of (R)-α-ethyl-2-oxo-1-pyrrolidineacetamide.

The processes may also enable the production of crude levetiracetam having a high chemical purity, i.e., comprising less than 0.2% by weight of impurities, preferably less than 0.12% by weight of impurities.

The processes may further enable the production of purified levetiracetam comprising less than 0.1% by weight of impurities.

The invention further relates to pharmaceutical compositions comprising levetiracetam made according to the inventive process, and a pharmaceutically acceptable carrier.

The invention further relates to a pharmaceutical formulation comprising levetiracetam and a pharmaceutically acceptable carrier, wherein the formulation comprises less than 0.2% by weight of impurities, preferably less than 0.1% by weight of impurities.

Pharmaceutical formulations may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

Pharmaceutical formulations of the present invention contain levetiracetam and one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dixoide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, levetiracetam and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Having thus described the various aspects of the present invention, the following examples are provided to illustrate specific embodiments of the present invention. They are not intended to be limiting in any way.

EXAMPLES

Example 1

Preparation of Crude Levetiracetam from L-ABA HCL in ACN

Anhydrous sodium sulfate 13.6 g (0.096 M) is added to dry acetonitrile (ACN) (96 ml) under vigorous stirring at 3–5 degrees C. and under a nitrogen blanket. (S)-2-aminobutanamide hydrochloride (L-ABA HCl) 11.08 g (0.08 M) is added. The mixture is stirred at 3–5 degrees C. for 30 minutes. Powdered KOH 17.23 g (0.28 M) is added. 4-chlorobutyryl chloride 12.41 g (0.088M) in 39 ml dry acetonitrile is added drop-wise over a period of about 30 minutes, while the temperature is kept under 5 degrees C. The reaction mixture is stirred while the temperature is kept under 5 degrees C. for a further 5 hrs. The insoluble matter is filtered off and washed with acetonitrile (15 ml). The filtrate and washing are evaporated in vacuo at 35–40 degrees C. The residue is recrystallized from 50 ml ethyl-acetate to give 9.6 g (Yield=70%) of product displaying 99% purity (crude product) by capillary GC; 99.65% L-isomer and 0.35% D-isomer (D-Levetiracetam) by dextrine based chiral capillary GC.

The amount of D-isomer was determined as follows: Column: Beta Dex325 capillary column 30 m×0.25 mm+0.25 micron thickness. Oven: 160 degrees C.; Carry gas: nitrogen, flow 1 ml/min.; Detector FID, 230 degrees C.; Injection: split. 150:1, 210 degrees C.; Sample: 1 microliter of 0.05% levitiracetam solution in methanol; RT of D-isomer: 34.5 min, levitiracetam-33.4 min.

Example 2

Preparation of Crude Levetiracetam from L-ABA HCL in ACN using a Drying Agent

L-ABA HCl 69.25 g (0.5 M) and powdered KOH 101.25 g (1.8 M) are added to a vigorously stirred suspension of powdered molecular sieves in 625 ml acetonitrile under nitrogen. The temperature is kept at about 10 degrees C. A solution of 4-chlorobutyryl chloride 77.5 g (0.5M) in acetonitrile 250 ml is added drop-wise. The temperature is kept under 20 degrees C. After 2 hrs, 1.25 liters of acetonitrile are added and the mixture is stirred for 1 hour and then filtered. The solid is washed with acetonitrile (25 ml). The combined filtrate and washes are evaporated in vacuo to yield a semi-solid oil 70 g, which upon crystallization from warm ethyl-acetate (150) ml leads to 60.5.5 g (72%) of levetiracetam 98.2% purity (crude product).

Example 3

Preparation of Crude Levetiracetam from L-ABA HCL in ACN with Neutralization

Anhydrous sodium sulfate 99.6 g is added with stirring into acetonitrile 700 ml under a nitrogen blanket. The temperature is set and maintained at 3–5 degrees during the reaction.

L-ABA HCl 69.25 g (0.5 M), followed by 124 g ground KOH are then introduced into the above mixed suspension. 4-chlorobutyryl chloride 77.6 g (0.55 M.) is added at a rate sufficient to keep the temperature at 3–5 degrees C. The reaction mixture is kept for 5 hrs under these conditions. The mixture is then neutralized with care to about pH 6 using concentrated HCl (32%). The mixture is filtered and washed twice with acetonitrile (total 400 ml). The filtrate and washes are combined and concentrated to a 500 ml solution which is filtered. Upon cooling, crude levetiracetam crystallizes displaying about 99% purity (HPLC). Recrystallization from warm ethyl acetate leads to 72 g (84%) of pure levetiracetam, displaying >99.5% isomeric purity by chiral capillary GC.

Example 4

Preparation of Crude Levetiracetam from L-ABA HCl in MTBE 6.92 g (0.05 M) L-ABA HCL and 10.12 g (0.18 M) ground KOH and 7.53 g (0.053M) of NaSO$_4$ are mixed vigorously in 62 ml methyl tert butyl ether (MTBE). The temperature is kept at 5 degrees C. A solution of 7.75 g (0.05 M) of 4-chlorobutyryl chloride (CBC) is added drop-wise. After 3 hours, the mixture is allowed to return to room temperature during 1 hour. The reaction mix is filtered and the solid is washed with a total of 87 ml MTBE to give a crude solid 6.5 g containing levetiracetam having a purity of 76% as per HPLC.

Example 5

Preparation of (S)-N-[1-aminocarbonyl)propyl]-4-chlorobutanamide (CBA) from ABA Base in MTBE 5.1 g (0.05 M) of ABA base and 9.75 g (0.1 M) of 2-hydroxypyridine are mixed vigorously in 60 ml of MTBE at 0–5 degrees C. A solution of 8.45 g (0.06 M) of CBC in 25 ml MTBE is added drop-wise over 30 minutes. The reaction is nearly completed after 2 hours but was left overnight for 17 hours. The reaction mix is filtered and the solid washed with 15 ml acetonitrile. The combined extracts are evaporated to a crude solid residue of 13 g which contains CBA having a purity of 91% as per HPLC.

Example 6

Preparation of Levetiracetam from CBA in the Presence of KI in MTBE 6.2 g (0.03 M) of CBA 2.5 g of ground KOH and 0.33 g (0.002 M) KI catalyst are stirred in MTBE vigorously at room temperature. After 4 hours, the mixture is filtered and the solid is washed twice with hot ethyl acetate. HPLC of the crude mixture indicates a purity of 95.9% of levetiracetam.

Example 7 (Comparative Example)

Preparation of Levetiracetam from CBA in MTBE without KI 6.2 g (0.03 M) of CBA 2.5 g of ground KOH are stirred vigorously at room temperature in MTBE. After 4 hours, the reaction mixture is filtered and the solid is washed twice with hot ethyl acetate. HPLC of the crude mix indicates 88.6% levetiracetam.

Example 8

PURIFICATION OF LEVETIRACETAM FROM VARIOUS SOLVENTS

| Solvent | Ratio Solvent:Material (ml/gr) |
|---|---|
| Acetone | 33 |
| Ethanol (absolute) | 17 |
| Ethyl-Acetate | 15 |
| Toluene | 25 |
| Toluene | 5 |
| Methylethyl Ketone (MEK) | 6 |
| CAN | 3.3 |
| Tetrahydrofuran (THF) | 6.5 |
| Isopropylalcohol (IPA) | 4.3 |
| Dichloromethane | 2.7 |
| Methanol | 1 |
| Ethanol | 2.3 |
| Chloroform | 1.7 |
| Nitromethane | 2 |
| Hexane | 100 |
| Toluene | 100 |
| MTBE | 100 |

Experimental Procedure:

A 100 ml flask is charged with 3 g of levetiracetam. Solvent is added in portions under slight reflux until total dissolution. Solutions are left to cool to room temperature for 5 hours and stored at 4 degrees C. for a further 16 hours. The crystalline material is filtered on buchner. The material is dried at 40–45 degrees C. under 100 mm vacuum.

Example 9

PURIFICATION OF LEVETIRACETAM FROM A MIXTURE OF TWO SOLVENTS

| Solvent A/Solvent B | Ratio Between Solvents | Ratio Solvent:Material (ml/gr) |
|---|---|---|
| MEK:Hexane | 1.4:1 | 40 |
| Ethyl-Acetate:Hexane | 3.6:1 | 39 |
| THF:Hexane | 1:1 | 37 |
| IPA:Hexane 1 | 1:2 | 30:2 |
| Dichloromethane:Hexane | 1:2 | 20 |
| Ethanol (absolute):Hexane | 1:2/5 | 14 |
| Chloroform:Hexane | 1:3/3 | 13 |
| Acetonitrile:Toluene | 1:1.2 | 18.3 |
| Methanol:Toluene | 1:16 | 39.7 |
| DMSO:Ethyl-Acetate | 1:8 | 15 |

Experimental Procedure:

A 100 ml flask is charged with 3 g. levetiracetam and the selected solvent is added in portions at about 40 degrees C., under stirring. The co-solvent is then added in portions until the solution is turbid. The suspension is left to cool under stirring to room temperature for 5 hours and left at 4 degrees C. for a further 16 hours. The crystalline material is filtered on buchner. The material is dried at 40–45 degrees C. under 100 mm vacuum.

Example 10

Preparation of Levetiracetam from L-ABA HCL in ACN using a Drying Agent 27.7 g (0.2 M) ABA HCl is added to 80 g (0.56 M) powdered $K_2CO_3$ in 500 ml ACN and the mixture is stirred at room temperature for 30 minutes and then cooled to about 0 degrees Celsius. A solution of 4-chlorobutyryl chloride, 31 g (0.22 M) in 100 ml of ACN is added to the mixture over a period of about 1 hour while the temperature is kept at between about 0–3 degrees Celsius. The reaction mixture is brought to room temperature and stirred for 2 hours. The temperature of the reaction mixture is raised to 30 degrees Celsius and 8.4 g (0.21 M) sodium hydroxide is added. After 90 minutes, another charge of 8.4 g sodium hydroxide is introduced and the mixture is stirred at 30 degrees Celsius for another 150 minutes. The suspension is filtered and the solid is washed with 0.25 liters of ACN. The filtrate and washes are combined and evaporated in vacuo to a solid which is crystallized from about 80 ml of hot ACN leading to a crude 26 g Levetiracetam (77% purity). Recrystallization of the crude levetiracetam from 170 ml hot ethylacetate gives 23.5 g of the final product.

What is claimed is:

1. A process for preparing (S)-α-ethyl-2-oxo-1-pyrrolidineacetamide (levetiracetam) comprising reacting (S)-2-amino-butanamide hydrochloride and 4-chlorobutyryl chloride in a solvent selected from the group consisting of acetonitrile and methyl tert-butyl ether, in the presence of a strong base and the absence of a tetrabutylammonium bromide catalyst, and recovering the crude levetiracetam.

2. A process for preparing (S)-α-ethyl-2-oxo-1-pyrrolidineacetamide which comprises cyclizing (S)-N-[1-(aminocarbonyl)propyl]-4-chlorobutanamide, in a solvent selected from the group consisting of acetonitrile and methyl tert-butyl ether, in the presence of a strong base and the absence of a tetrabutylammonium bromide catalyst, and recovering the crude levetiracetam.

3. A process of claim 2, wherein the reaction is performed in the absence of a catalyst.

4. A process for preparing (S)-α-ethyl-2-oxo-1-pyrrolidineacetamide (levetiracetam) comprising reacting (S)-2-amino-butanamide hydrochloride and 4-chlorobutyryl chloride, in an inert solvent, in the absence of a catalyst, and recovering the crude levetiracetam.

5. The process of claim 4, wherein the reaction takes place in the presence of a strong base.

6. The process of claim 4, wherein the inert solvent is selected from the group consisting of acetonitrile and methyl tert-butyl ether.

7. The process of claim 1, wherein the crude levetiracetam comprises less than about 0.4% by weight of (R)-α-ethyl-2-oxo-1-pyrrolidineacetamide.

8. The process according to claim 1, wherein the crude levetiracetam comprises less than about 0.2% by weight of impurities.

9. The process of claim 1, further comprising purifying the crude levetiracetam by crystallizing or recrystallizing it from an organic solvent or a mixture of organic solvents to obtain purified levetiracetam.

10. The process of claim 9, wherein the organic solvent is selected from the group consisting of ethanol, ethyl acetate, toluene, methylethyl ketone, tetrahydrofuran, isopropylalcohol, dichloromethane, methanol, nitromethane, hexane, and methyl tert-butyl ether.

11. The process of claims 1, wherein the strong base is present in an amount of at least about 3 molar equivalents based on the amount of (S)-2-amino-butanamide hydrochloride.

12. The process of claim 1, wherein the reaction temperature is maintained at between about −15 degrees Celsius and about +15 degrees Celsius.

13. The process of claim 1, wherein the reaction takes place in the presence of a drying agent.

14. The process of claim 13, wherein the drying agent is selected from the group consisting of magnesium sulphate, molecular sieves, potassium carbonate, sodium carbonate, and sodium sulphate.

15. The process of claim 14, wherein the reaction temperature is maintained at between about 0 degrees Celsius and about +5 degrees Celsius.

16. The process of claim 14, further comprising purifying the crude levetiracetam by recrystallizing it from an organic solvent or a mixture of organic solvents to obtain purified levetiracetam.

17. The process of claim 16, wherein the organic solvent is selected from the group consisting of ethanol, ethyl acetate, toluene, methylethyl ketone, tetrahydrofuran, isopropylalcohol, dichloromethane, methanol, nitromethane, hexane, and methyl tert-butyl ether.

18. The process of claim 16, wherein the organic solvent is ethyl acetate.

19. The process of claim 13, wherein the drying agent is potassium carbonate.

20. The process of claim 13, wherein the drying agent is molecular sieves.

21. The process of claim 14, wherein the drying agent is sodium sulphate.

22. The process of claim 1, further comprising adding an acid or a mixture of acids to the completed reaction mixture to adjust the pH to less than about 8.

23. The process of claim 22, wherein the pH is adjusted to less than about 7.

24. The process of claim 22, wherein the acid or mixture of acids is selected from the group consisting of a mixture of hydrochloric acid and acetic acid, and formic acid.

25. A process for preparing (S)-α-ethyl-2-oxo-1-pyrrolidineacetamide, comprising reacting (S)-2-amino-butanamide hydrochloride and 4-chlorobutyryl chloride, in an inert solvent and in the absence of a tetrabutylammonium bromide catalyst, and recovering the crude levetiracetam.

26. A process for preparing (S)-α-ethyl-2-oxo-1-pyrrolidineacetamide, which comprises cyclizing (S)-N-[1-(aminocarbonyl)propyl]-4-chlorobutanamide, in an inert solvent and in the absence of a tetrabutylammonium bromide catalyst, and recovering the crude levetiracetam.

* * * * *

UNITED STATES PATENT AND TRADEMARK OFFICE
CERTIFICATE OF CORRECTION

PATENT NO. : 7,132,552 B2
APPLICATION NO. : 10/771821
DATED : February 3, 2004
INVENTOR(S) : Ben-Zion Dolitzky et al.

It is certified that error appears in the above-identified patent and that said Letters Patent is hereby corrected as shown below:

Column 3, line 30, change "...bucally..." to -- buccally --

Column 3, line 52, change "...pregelitinized..." to -- pregelatinized --

Column 3, line 64, change "...carbopol..." to -- Carbopol® --

Column 4, line 65, change "...ethylcellulose..." to -- ethyl cellulose --

Column 5, line 12, change "...guconic acid..." to -- gluconic acid --

Column 5, line 13, change "...guconate..." to -- gluconate --

Column 5, line 31, change "...losenges..." to -- lozenges --

Column 6, line 32, change "...dextrine based..." to -- dextrin-based --

Column 6, line 57, change "...60.5.5 g..." to -- 60.55 g --

Column 6, line 66, change "...3-5 degrees..." to -- 3-5 degrees C --

Column 7, line 23, change "...methyl tert butyl ether..." to -- methyl tertbutyl ether --

Column 8, line 50, change "30:2" to -- 30 --

UNITED STATES PATENT AND TRADEMARK OFFICE
CERTIFICATE OF CORRECTION

PATENT NO. : 7,132,552 B2
APPLICATION NO. : 10/771821
DATED : February 3, 2004
INVENTOR(S) : Ben-Zion Dolitzky et al.

It is certified that error appears in the above-identified patent and that said Letters Patent is hereby corrected as shown below:

Column 8, line 51, change "Dichioromethane:Hexane" to
-- Dichloromethane:Hexane --

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,132,552 B2                                    Page 1 of 2
APPLICATION NO. : 10/771821
DATED              : November 7, 2006
INVENTOR(S)        : Ben-Zion Dolitzky et al.

It is certified that error appears in the above-identified patent and that said Letters Patent is hereby corrected as shown below:

Column 3, line 30, change "...bucally..." to -- buccally --

Column 3, line 52, change "...pregelitinized..." to -- pregelatinized --

Column 3, line 64, change "...carbopol..." to -- Carbopol® --

Column 4, line 65, change "...ethylcellulose..." to -- ethyl cellulose --

Column 5, line 12, change "...guconic acid..." to -- gluconic acid --

Column 5, line 13, change "...guconate..." to -- gluconate --

Column 5, line 31, change "...losenges..." to -- lozenges --

Column 6, line 32, change "...dextrine based..." to -- dextrin-based --

Column 6, line 57, change "...60.5.5 g..." to -- 60.55 g --

Column 6, line 66, change "...3-5 degrees..." to -- 3-5 degrees C --

Column 7, line 23, change "...methyl tert butyl ether..." to -- methyl tertbutyl ether --

Column 8, line 50, change "30:2" to -- 30 --

UNITED STATES PATENT AND TRADEMARK OFFICE
CERTIFICATE OF CORRECTION

PATENT NO. : 7,132,552 B2
APPLICATION NO. : 10/771821
DATED : November 7, 2006
INVENTOR(S) : Ben-Zion Dolitzky et al.

It is certified that error appears in the above-identified patent and that said Letters Patent is hereby corrected as shown below:

Column 8, line 51, change "Dichioromethane:Hexane" to
-- Dichloromethane:Hexane --

This certificate supersedes the Certificate of Correction issued June 30, 2009.

Signed and Sealed this

Twenty-eighth Day of July, 2009

JOHN DOLL
*Acting Director of the United States Patent and Trademark Office*